(12) United States Patent
Perkins

(10) Patent No.: US 6,334,876 B1
(45) Date of Patent: Jan. 1, 2002

(54) SAFETY SUCTION VALVE

(76) Inventor: Dale Perkins, 1061 Lakewood, Twin Falls, ID (US) 83301

( * ) Notice: Subject to any disclaimer, the term of this patent is extended or adjusted under 35 U.S.C. 154(b) by 0 days.

(21) Appl. No.: 09/305,703

(22) Filed: May 5, 1999

Related U.S. Application Data

(60) Provisional application No. 60/084,368, filed on May 5, 1998.

(51) Int. Cl.[7] .................................................. A61F 2/62
(52) U.S. Cl. .......................................... 623/34; 623/38
(58) Field of Search ...................................... 623/33–38

(56) References Cited

U.S. PATENT DOCUMENTS

| | | |
|---|---|---|
| 1,586,015 A | 5/1926 | Underwood |
| 2,530,285 A | 11/1950 | Catrainis |
| 2,533,404 A | 12/1950 | Sharp et al. |
| 2,569,790 A | 10/1951 | White et al. |
| 2,790,180 A | 4/1957 | Hauser |
| 2,897,512 A | 8/1959 | Sackett |
| 4,634,446 A | 1/1987 | Kristinsson |
| 5,007,937 A | 4/1991 | Fishman et al. |
| 5,201,774 A | 4/1993 | Greene |
| 5,376,131 A | 12/1994 | Lenze et al. |
| 5,507,834 A | 4/1996 | Laghi |
| 5,507,837 A * | 4/1996 | Laghi .......................... 623/33 |
| 5,658,353 A | 8/1997 | Layton |
| 5,709,017 A | 1/1998 | Hill |
| 5,888,215 A | 3/1999 | Roos et al. |
| 5,888,234 A * | 3/1999 | Littig ........................... 623/33 |
| 5,904,722 A * | 5/1999 | Caspers ........................ 623/33 |
| 6,106,559 A * | 8/2000 | Meyer .......................... 623/33 |

* cited by examiner

*Primary Examiner*—Bruce Snow
(74) *Attorney, Agent, or Firm*—Ken J. Pedersen; Barbara S. Pedersen

(57) ABSTRACT

The present invention describes a safety suction valve that releasably secures a residual limb to an artificial limb. The safety suction valve synchronously actuates a latch mechanism and a valve mechanism, thereby providing superior retention of a residual stump in a stump socket and resulting in ease of donning and doffing of a stump socket by an amputee. The consolidation of the latch and valve mechanisms of the safety suction valve is an improved feature over conventional artificial limb supporting devices. This consolidation provides a redundant system for reliably suspending an artificial limb from a residual limb. The invention also includes an alignment kit and prescribes an alignment method which result in an accurate and reliable alignment between the residual and artificial limbs

3 Claims, 13 Drawing Sheets

FIG. 18A  FIG. 18C  FIG. 18B

SAFETY SUCTION VALVE

This application claims priority to Provisional Application No. 60/084,368 filed May 5, 1998, under 35 U.S.C. § 119 (e).

BACKGROUND OF THE INVENTION

1. Field of the Invention

The present invention relates generally to prosthetics, and, more specifically to a safety suction valve that synchronously actuates a latch mechanism and valve mechanism during donning/doffing of a stump socket and during use of a prosthesis, and an alignment kit/method that allows easy and inexpensive alignment of the prosthesis.

2. Background of the Related Art

It has long been appreciated that differential air pressure or "suction" may be utilized to retain or "suspend" a prosthetic limb on an amputee's stump. Gravitational and other forces tend to cause separation between the prosthetic limb and the patient's residual extremity during use. This happens, for example, during the swing phase of gait, when a prosthetic leg is additionally subjected to centrifugal forces. Patients have routinely worn a variety of belts, straps, cuffs and harnesses to retain their prosthetic limbs against separation from the residual limb. But such devices are inconvenient and tend to cause chafing against the patient's body giving rise to sores and abrasions.

The manner in which an artificial limb is suspended and/or attached to the residual limb determines the amount of control an amputee has over the prosthesis. Suction suspension typically involves the utilization of a socket liner and a "hard" stump socket. The liner, which is usually fabricated from silicone, fits snugly over the residual limb and is, in turn, enveloped by the socket. A region of negative pressure between the liner-sheathed stump and the interior of the socket serves to hold the prosthesis upon the limb during use. The suspension method is very advantageous for the amputee. It gives the amputee the ability to better control the prosthesis and provides for useful sensory or proprioceptive feedback. Suction suspension also makes a prosthesis feel lighter as compared to other forms of suspension.

Some form of valve means is usually employed to regulate the air pressure in the socket such that undesirable pressure differentials do not prevent or complicate the donning and doffing of the socket. The valve means also maintains the suction or negative pressure once the socket has been satisfactorily clad. During donning, the patient's liner-sheathed stump is inserted into the socket. At some stage or stages during the insertion the socket liner will form a roughly circumferential air-tight seal through contact with the hard socket. As the patient's stump is inserted further into the socket, air pressure builds up under the stump. The provision of valve means permits air to escape from the socket until the pressure inside the socket equalizes with the ambient pressure and, hence, allows the stump to be fully inserted inside the socket. As a result, when the stump is completely inserted in the socket, the air pressure is equal inside and outside the socket. The valve means are now closed so that no air is allowed to flow into the distal end of the stump socket. Any tendency to remove the stump from the socket would increase the space between the inner socket wall and the stump, reducing the pressure inside the socket, since external air is unable to enter. The difference between the ambient pressure and the reduced pressure within the socket creates a "suction" effect that acts to maintain the socket on the stump. In this manner, the prosthesis is "suspended" on the patient's stump. During removal of the stump from the socket (or doffing) the valve means are opened or adjusted so as to equalize the ambient pressure and the pressure inside the socket, thus dissipating the "suction" effect and allowing for an easy removal of the stump.

There are several suction valves available in the market today. One class of valves consists of a valve and seat combination in which the valve and seat are threadably engaged. The seat is side-mounted on to the distal end of the socket and the valve/seat assembly is usually disengaged during donning and doffing. Another type of suction valve is an automatic air expulsion one-way valve which automatically exhausts air from the socket during donning, thereby permitting insertion of the stump into the socket. The one-way valve may be manually operated, during doffing, to allow air to pass from the outside into the interior of the socket.

Though the principle of employing "suction" for "suspending" an artificial limb is quite clear, there are some associated practical problems. One of these is the difficulty in providing a reliable and permanently effective seal at the proximal open end of the socket This issue being important in maintaining the reduced pressure inside the socket. Moreover, in some instances it is doubtful whether the suspending suctional force can independently support the weight of the lower limb prosthesis. This is problematic from a safety stand-point, because if the suspension means fail, and there is no redundant or back-up support mechanism, the artificial limb could detach from the patient's stump.

U.S. Pat. No. 5,376,131 to Lenze et al. sets forth a socket with an elastic diaphragm that sealingly engages a patient's stump, and hence attempts to provide an effective seal, but the local constriction due to such a tightly fitting diaphragm can result in impairment of circulation in the amputee's residual limb. Suspension sleeves, which are substantially elongated bands fabricated from a resilient material and envelop part of the stump and part of the outer socket, have been used to provide complementary mechanical support and may additionally function in some capacity as a sealing means. But since these sleeves constrictingly grip the residual limb over a wide region they can limit limb movement or otherwise be uncomfortable.

A different approach to tackling this problem has led to the design of a socket liner which is attachable at its distal end to a socket or artificial limb. In this manner, the liner is mechanically secured and can provide additional suspension, if needed, and/or can play the role of a backup suspension means. Typically, the socket liner is equipped with a detachable attachment component, at its distal end, which mates with a locking device and hence secures the residual limb to an artificial limb. The locking devices generally employ a spring-loaded clutch mechanism or a pin-lock mechanism to lock on to the liner attachment component. This attachment component is either a barb-shaped structure or a frictionally-retained pin. These attachment components can lock in a plurality of positions which affects the overall length of the prosthesis. Though this may be advantageous in some cases, it can make it difficult for the patient to consistently achieve the same prosthetic configuration when the residual limb and the artificial limb are articulated. It should further be noted that in this mode of limb suspension the locking means and the valve means are autonomous entities which are separately invasive and additive in weight on the distal end of the socket.

Another type of suspension device which is in widespread use today is known as a roll-on suction socket. The suction socket, which is typically fabricated from silicone, is basically a long tubular structure with one open end. The distal end of the suction socket is attachable to a prosthesis via an attachment component and a locking device employing the same principle and design described above. During donning, the suction socket is turned inside out and rolled on to the residual stump in a fashion basically the same as donning a condom, being careful to avoid trapping of any air between the skin of the limb and the suction socket. Since the suction socket creates/destroys a partial vacuum at its distal end during rolling-on/rolling-off of the socket the function of a valve means are intrinsically incorporated into the donning/doffing technique. Thus, it would appear that the suction socket is a simple and effective device to suspend a prosthesis. But, this can be misleading because the suction socket may not be sealingly gripped by the hard socket, thereby converting the suction socket for all practical purposes into a "traction" socket. Thus, the prosthesis is suspended onto the residual limb by a combination of the frictional adhesive traction of the suction socket and the locking retention due to the locking device. This skin traction causes an undesirable "tethering" effect by pulling on the skin, thereby creating multiple skin problems, especially since the suction socket is usually not custom-fitted and is generally a relatively long tube which contacts a large area of skin on the residual limb. The length of the tube can also interfere with the mobility of the residual limb, especially in the case of below-knee amputees.

Once a desired suspension device has been assimilated into the prosthesis, the prosthesis must be laterally aligned with respect to the residual limb. A typical conventional method for alignment of a prosthesis involves the use of a multi-axis slide mechanism which allows adjustment with two degrees of freedom. The alignment is reached by adjusting the relative horizontal positioning between two plates, one of which is attached to the distal end of the socket (or to the locking device) and the other to the top end of the artificial limb. Each plate has a centrally located slot and the slots are perpendicularly oriented to one another. Once the proper alignment has been ascertained a fastening means, such as a nut/bolt/washer combination couples the residual limb with the artificial limb. Such an alignment mechanism can be hazardous. During use of the prosthesis the interface between the socket and the artificial limb is subjected to stresses and moments that can result in relative motion between the alignment plates, thus misaligning the prosthesis. Moreover, in extreme cases, the coupling plates may become laxly connected or totally unfastened, thereby, placing the patient at risk of harm. Also, the conventional alignment device not only adds excess weight to the prosthesis, but also adds to the cost since it is a complicated, intricate device which is typically fabricated from titanium. Further the size of this alignment device undesirably adds to the overall length of the prosthesis, which can be problematic when accommodating long stump lengths.

Conventional techniques have not been able to provide an effectual solution to gainfully employing the benefits of suction suspension in prosthetic devices. Several issues, in the field of prosthetics, related to suspension of an artificial limb and alignment between the residual and artificial limbs need to be addressed. These include improving the retention of the stump in the socket without sacrificing the patient's comfort and without comprising on expense, weight and simplicity of use of the prosthesis. Moreover, there is also a need for a safe and convenient alignment kit/method to permit reliable, slip-free alignment and articulation between the residual stump and the artificial limb.

SUMMARY OF THE INVENTION

The present invention in one embodiment provides a safety suction valve that overcomes some or all of the afore-mentioned disadvantages by incorporating a redundant support scheme for securing a residual limb to an artificial limb. The safety suction valve substantially synchronously activates a latch mechanism and a valve mechanism, thereby providing superior retention of a residual stump in a stump socket and resulting in ease of donning and doffing of a stump socket by an amputee. The consolidation of the latch and valve mechanisms is an improved feature of the present invention. The invention in one embodiment also includes an alignment kit and prescribes an alignment method which result in a reliable and secure alignment between a residual limb and an artificial limb.

In accordance with one preferred embodiment of the invention a safety suction valve is provided comprising a locking pin, a plunger and a base. The top part of the locking pin is sized and shaped so as to be attachable to the distal end of a socket liner and the bottom part of the locking pin is latchable in a first cavity of the base. The bottom part of the locking pin has a medial section that is recessed, and is preferably substantially hourglass-shaped, so as to mate with a corresponding latch mechanism. The plunger is spring-loaded and is resident in a second cavity of the base and has a medial section that is recessed, and is preferably substantially hourglass-shaped, so as to lockingly mate with the recess of the locking pin. The plunger has a released or at rest state which dually latches the locking pin to the base and seals the open end of the second cavity of the base. When the safety suction valve is in use with a lower limb prosthesis, this released state provides a redundant support system for suspending the prosthesis by mechanically latching the locking pin and by maintaining a suspending suctional force between the stump and the stump socket. Conversely, the plunger has a depressed state that concurrently unlatches the locking pin and releases the suction.

In accordance with another preferred embodiment of the invention a safety suction valve is provided comprising a locking pin, a base, and a plunger assembly. The plunger assembly includes a latching plate, a plunger and a plunger mount. The top part of the locking pin is sized and shaped so as to be attachable to the distal end of a socket liner and the bottom part of the locking pin is latchable in the base. The bottom part of the locking pin has one or more recesses to lockingly mate with a protrusion of the latching plate. The plunger is spring-loaded and in resilient communication with the latching plate. The plunger has a released or at rest state which dually latches the locking pin to the base and seals a cavity of the plunger mount. When the safety suction valve is in use with a lower limb prosthesis, this released state provides a redundant support system for suspending the prosthesis by mechanically latching the locking pin and by maintaining a suspending suctional force between the stump and the stump socket. Conversely, the plunger has a depressed state that concurrently unlatches the locking pin and releases the suction.

In one preferred embodiment, the locking pin of the safety suction valve of the present invention includes one latching recess so that it latches inside the valve in a substantially repeatable single position. This is desirable when the patient needs to repeatedly and consistently achieve substantially the same prosthetic configuration when the residual and artificial limbs are articulated. In other preferred embodiments, the locking pin can include more than one recess so that it can latch at a plurality of positions in the valve, as dictated by the particular needs of the patient.

The present invention in one preferred embodiment also provides an alignment kit which includes a plurality of alignment couplers and a base having a low-profile stem. The stem may be incorporated with the base of a safety suction valve or, alternatively, may be part of an autonomous base member. Each alignment coupler has a substantially central hole to non-rotatably mate with the stem of the base. The alignment coupler hole may be situated in a multitude of eccentric locations, thereby allowing for a plurality of alignment options between the residual and artificial limbs which in turn permits an accurate alignment.

Preferably, an embodiment of the invention utilizes a laminated socket which securely substantially envelops the alignment coupler and the base, hence ensuring optimum coupling strength between the stump socket, base and alignment coupler. The alignment coupler is securably attachable to a lower limb prosthesis. Preferably, the alignment coupler is fabricated from a low-cost, light-weight, durable material such as aluminum though other materials may be employed with efficacy. The alignment coupler preferably has a modest thickness. Advantageously, these desirable features add minimally to the overall cost, weight and length of the prosthesis.

The present invention in one preferred embodiment also prescribes a method of aligning a stump to a lower limb prosthesis. The method includes the step of attaching a test socket to the lower limb prosthesis via an adjustable coupler. The stump which is sheathed with a socket liner is placed in the test socket. The required relative offset between the stump and the lower limb prosthesis is determined utilizing the adjustable coupler. The test socket is detached from the lower limb prosthesis and the adjustable coupler. An alignment coupler is selected based on the required relative offset between the stump and the lower limb prosthesis. A laminated stump socket is then fabricated. The lamination of the stump socket securely substantially envelops the base and the alignment coupler.

The preferred alignment method described herein, advantageously, permits prealignment of the prosthesis before the lamination during a single patient examination. Conventional alignment transfer may require the lamination to be performed before the alignment, and this can undesirably result in two examinations of the patient.

For purposes of summarizing the invention and the advantages achieved over the prior art, certain objects and advantages of the invention have been described herein above. Of course, it is to be understood that not necessarily all such objects and advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 18A is a front elevational view of the latching plate of FIG. 13;

FIG. 18B is a back elevational view of the latching plate of FIG. 13;

FIG. 18C is a top plan view of the latching plate of FIG. 13;

DETAILED DESCRIPTION OF THE PREFERRED EMBODIMENTS

Figure 1:
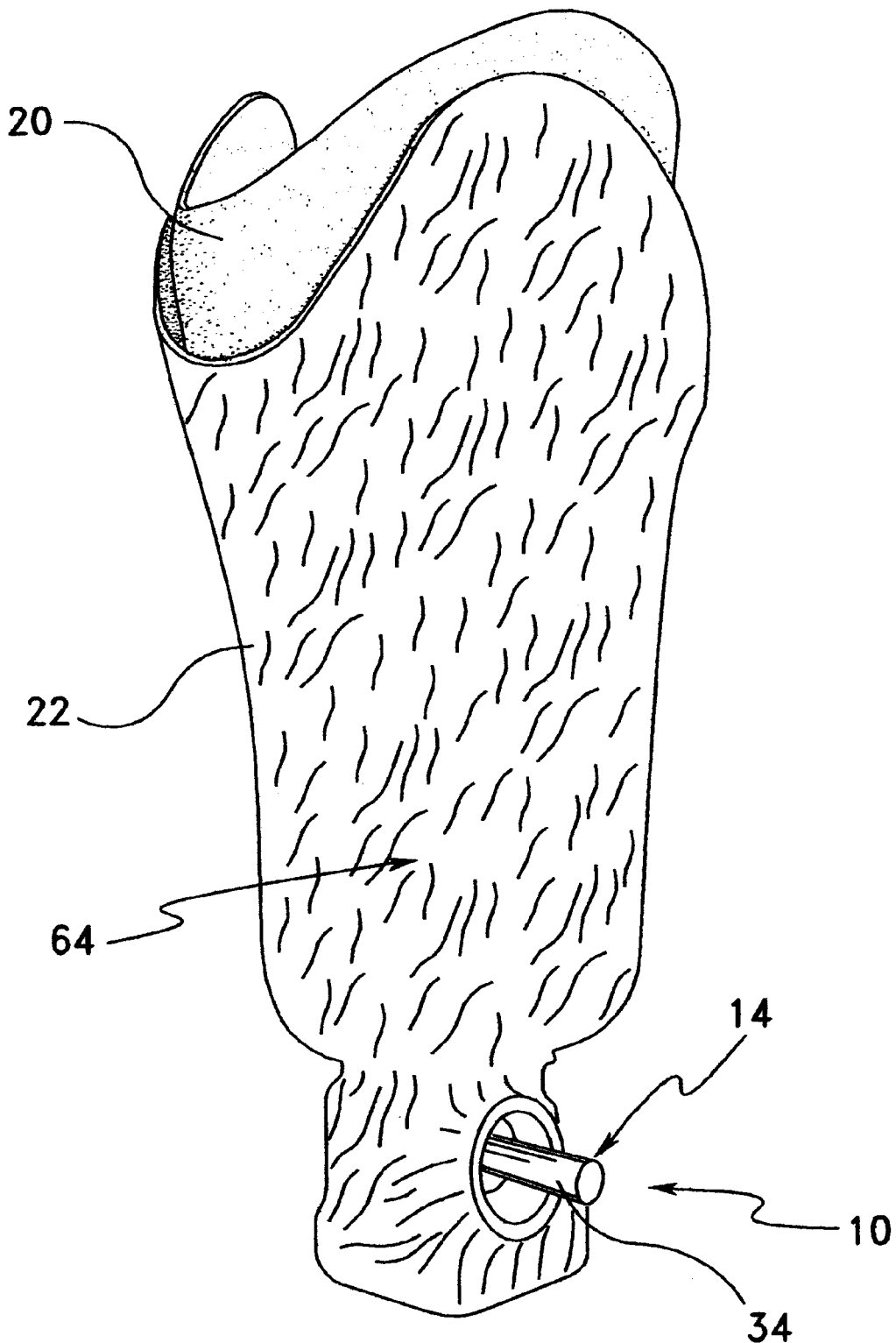
FIG. 1 illustrates a safety suction valve attached to a prosthesis in accordance with one preferred embodiment of the present invention.
Figure 2:
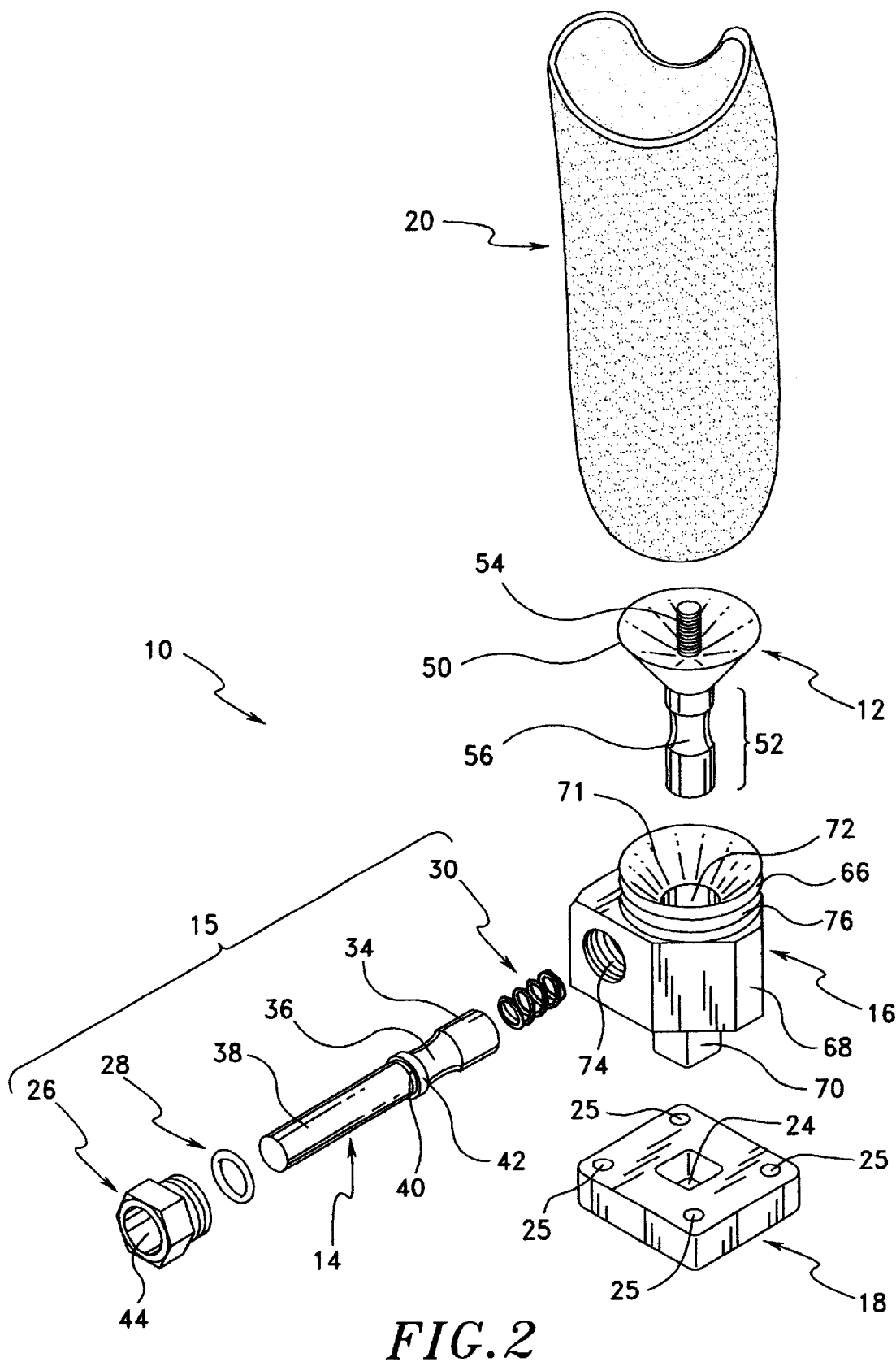
FIG. 2 is an exploded perspective view of the safety suction valve of FIG. 1.

FIGS. 1 and 2 show one preferred embodiment of a suction valve or lock 10 constructed and assembled in accordance with the teachings of the present invention. FIG. 1 illustrates a preferred manner in which the suction valve 10, attached to a socket liner 20, is assimilated into a laminated stump socket 22.

As best shown in FIG. 2, the safety suction valve 10 generally comprises a locking pin 12, a plunger 14 and a base 16. Preferably, the top part 50 of the locking pin 12 has a substantially frusto-conical shape with a concave upper surface in which a screw 54 is embedded. The screw 54 can threadably engage a connector 58 (see FIG. 3) at the distal end 59 of the socket liner 20 and, hence, couple the locking pin 12 to the socket liner 20. The bottom part 52 of the locking pin 12 is substantially cylindrical at each end and has a recessed medial portion 56 that is tapered down to form an annular recess, groove or notch, preferably hourglass-shaped. The bottom part 52 of the locking pin 12 is latchable in the base 16 as will be discussed at greater length later herein. Preferably, the locking pin 12 is fabricated from a light-weight durable material, for example, delrin plastic, although various other suitable materials may be used with efficacy, as required or desired, such as aluminum, titanium, Nylon or other plastics, among others. Preferably, the locking pin 12 has a full-span length of about 1.625 inches and a maximum diameter of about 1.375 inches, with the bottom part 52 having a maximum diameter slightly less than approximately 0.5 inches. The recessed medial portion of the bottom part 52 preferably has a length of about 0.375 inches.

Preferably, the socket liner 20 (FIGS. 2 and 3) is fabricated from silicone and has a thickened distal end 59. A connector 58 is preferably embedded in the distal end 59 of the socket liner 20 and has a threaded part 60 which is exposed and is threadably engageable with the screw 54 of the locking pin 12. Preferably, the socket liner 20 is customized to the shape and size of a patient's residual limb, although suitable commercially available liners may also be substituted, if desired. Advantageously, custom-fitting the socket liner 20 ensures that the liner height will be optimally controlled, thereby preventing or minimizing the "tethering" effect, of the socket liner 20 on the residual limb, since an unnecessarily large area of skin will not be exposed to the socket liner 20.

Figure 4:
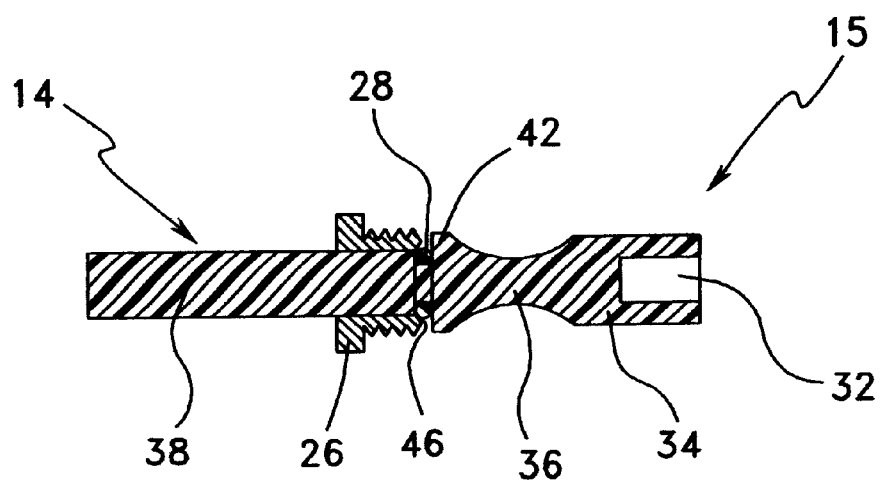
FIG. 4 is a sectional view of a plunger assembly of the safety suction valve of FIG. 1.

The plunger 14 (FIGS. 2 and 4) of the safety suction valve 10 is preferably spring-loaded. The plunger 14, an O-ring 28, a fitting 26 and a coil spring 30 preferably form a spring-loaded plunger assembly 15. Preferably, the coil spring 30 is at least partially resident in a cavity 32 in the substantially cylindrical anterior section 34 of the plunger 14. The medial section 36 of the plunger 14 is tapered down to form an annular recess or notch, preferably hourglass-shaped. Preferably, the posterior section 38 of the plunger 14 is substantially cylindrical with a groove 40 accommodating the O-ring 28 and a lip 42 adjacent to the medial section 36. Preferably, the plunger 14 is fabricated from a light-weight durable material, for example, delrin plastic, although various other suitable materials may be used with efficacy, as required or desired, such as aluminum, titanium, Nylon or other plastics, among others. Preferably, the plunger 14 has a full-span length of about 2.5 inches, with the anterior section 34 having a diameter slightly less than approximately 0.5 inches. The posterior section 38 of the plunger 14 preferably has a diameter slightly less than approximately 0.375 inches and a length of about 1.625 inches, though the length of the posterior section is adjustable to enhance the compactness of the safety suction valve 10. Preferably, the recessed medial section 36 of the plunger 14 has a length of about 0.375 inches. The coil spring 30 preferably has an outer diameter of about 0.25 inches and a free length of about 0.75 inches.

The plunger 14 (FIGS. 2 and 4) is preferably banded by the fitting 26 (FIGS. 2 and 4) with a through hole 44 which has a diameter slightly larger than the diameter of the posterior section 38 of the plunger 14 but smaller than the diameter of the lip 42 of the posterior section 38 of the plunger 14. The through hole 44 of the fitting 26 permits substantially coaxial relative motion between the fitting 26 and the posterior section 38 of the plunger 14, and also provides a small gap or clearance for air flow. The fitting 26 preferably has a chamfer 46 that allows sealed positive contact between the fitting 26 and the O-ring 28, and male threads which permit attachment of the fitting 26 to the base 16. Preferably, the fitting 26 is fabricated from a durable light-weight metal such as brass but many other materials may also be employed with efficacy, as required or desired, such as stainless steel, aluminum, titanium, delrin, Nylon or other plastics, among others.

The base 16 (FIG. 2) preferably includes an upper part 66, a middle part 68 and a stem 70 at the lower surface of the middle part 68. The upper part 66 of the base 16 preferably has a substantially cylindrical exterior surface with a groove 76 which facilitates interfacement of the base 16 with distal end of the stump socket 22. Preferably, the upper part 66 has a substantially bowl-shaped interior surface 71 for receiving the top part 50 of the locking pin 12. The surface 71 terminates in a first cylindrical cavity 72 which resides inside the middle part 68 and the stem 70 of the base 16. The diameter of the first cylindrical cavity 72 is preferably slightly larger than the maximum diameter of the bottom part 52 of the locking pin 12 so that the bottom part 52 is insertable into the first cylindrical cavity 72, and a gap or clearance is provided for air flow.

As can be seen in FIG. 2, the middle part 68 of the base 16 preferably has a substantially hexagonal outer cross-section and includes a second cylindrical cavity 74. The axis of symmetry of the second cylindrical cavity 74 is preferably offset and substantially perpendicular to the axis of symmetry of the first cylindrical cavity 72. The first cylindrical cavity 72 and the second cylindrical cavity 74 are in communication through a concavo-convex intersection plane. The open end of the second cylindrical cavity 74 is threaded to threadably engage the fitting 26. The diameter of the second cylindrical cavity 74 is at least slightly larger than the diameter of the anterior section 34 of the plunger 14. This allows the plunger to be displaceable within the second cylindrical cavity 74, and also provides a gap or clearance for air flow. The plunger 14 with the spring 30 resident in the cavity 32 is insertable into the second cylindrical cavity 74 and is sealably securable by use of the O-ring 28 and fitting 26. Preferably, the base 16 has a maximum length dimension of about 1.875 inches and maximum lateral dimensions of about 1.625 inches×1.625 inches. The first cylindrical cavity 72 and the second cylindrical cavity 74 preferably have diameters of about 0.5 inches and lengths of about 1.375 inches. Preferably, the base 16 is fabricated from a light-weight durable material, for example, delrin plastic, although various other materials may also be used with efficacy, as required or desired, such as aluminum, titanium, Nylon or other plastics, among others.

Figure 5A:
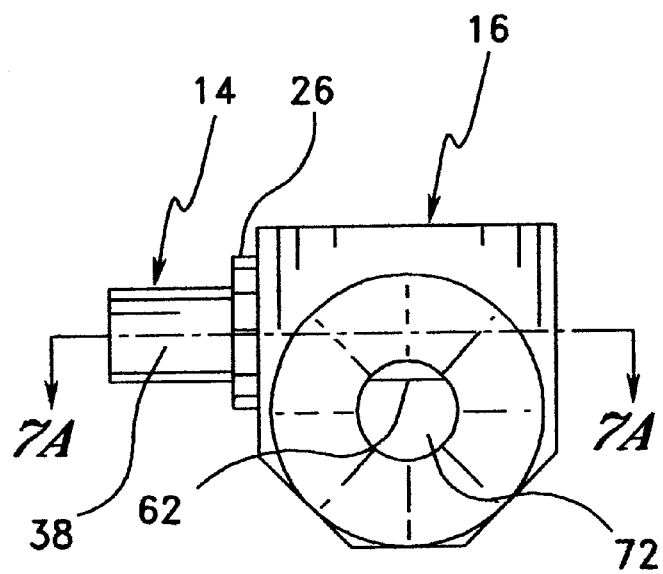
FIG. 5A is a top plan view of the safety suction valve of FIG. 1 with the locking pin removed to illustrate a "released" plunger position.
Figure 6A:
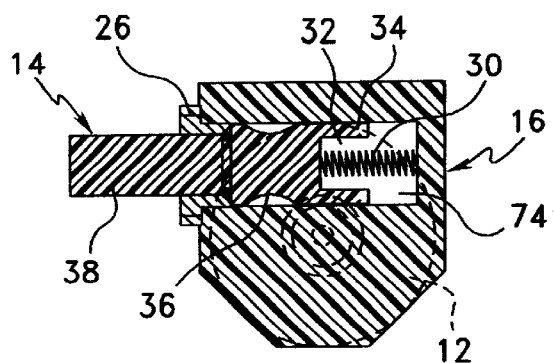
FIG. 6A is a sectional view along line 6A—6A of FIG. 7A.
Figure 7A:
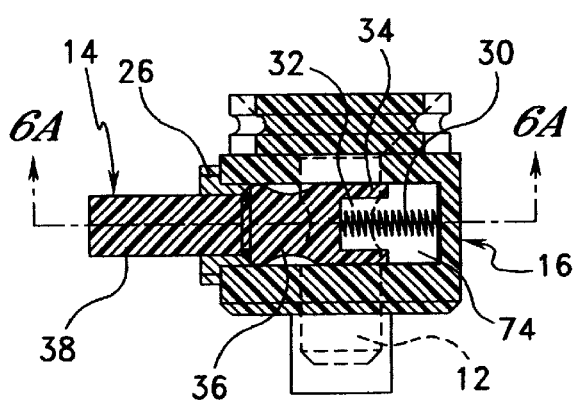
FIG. 7A is a sectional view along line 7A—7A of FIG. 5A.

The plunger 14 has a "released "state, as shown in FIGS. 5A, 6A and 7A, in which a portion 62 (shown in FIG. 5A) of the anterior section 34 of the plunger 14 resides in the concavo-convex intersection plane formed between the first cylindrical cavity 72 and the second cylindrical cavity 74—it should be noted that FIGS. 6A and 7A depict the locking pin 12 in phantom. The released state is the normal or at rest state of the plunger 14 of the safety suction valve 10. The portion 62 of the anterior section 34 of the plunger 14, in the released state, presents a physical obstruction to the insertion/removal of the bottom part 52 of the locking pin 12 into/from the first cylindrical cavity 72. In the released state of the plunger 14 the coil spring 30 is preferably slightly compressed to provide a biasing force on the plunger 14. This biasing force permits the chamfer 46 of the fitting 26 to make sealed positive contact with the O-ring 28, hence sealing the open end of the second cylindrical cavity 74.

Figure 5B:
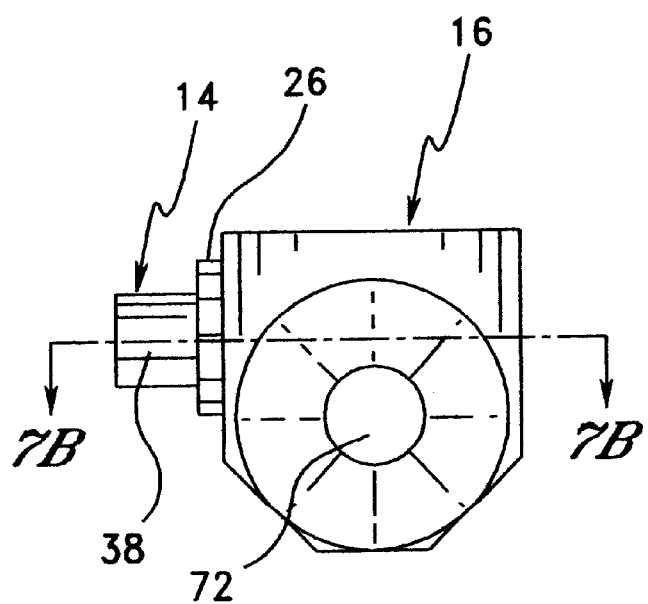
FIG. 5B is a top plan view of the safety suction valve of FIG. 1 with the locking pin removed to illustrate a "depressed" plunger position.
Figure 6B:
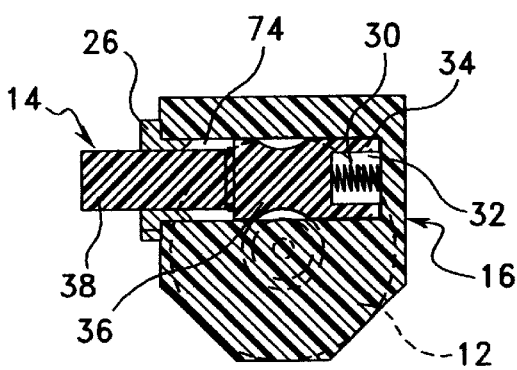
FIG. 6B is a sectional view along line 6B—6B of FIG. 7B.
Figure 7B:
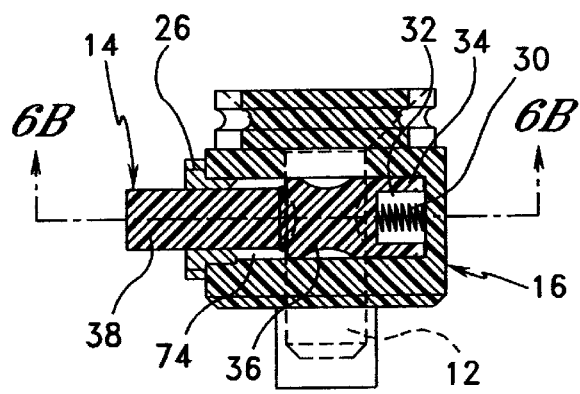
FIG. 7B is a sectional view along line 7B—7B of FIG. 5B.

The plunger 14 has a "depressed" state, as shown in FIGS. 5B, 6B and 7B in which the recessed medial section 36, preferably hourglass-shaped, of the plunger 14 is substantially affiliated with the concavo-convex intersection plane formed between the first cylindrical cavity 72 and the second cylindrical cavity 74—it should be noted that FIGS. 6B and 7B depict the locking pin 12 in phantom. The depressed state is achieved by depressing, preferably manually, the plunger 14 of the safety suction valve 10. In the depressed state of the plunger 14 the coil spring 30 is preferably substantially compressed as the plunger 14 reaches its end-of-travel within the second cylindrical cavity 74. With the plunger 14 in the depressed state the recess 36 aligns with the first cylindrical cavity 72 such that there is no physical obstruction to the insertion/removal of the bottom part 52 of the locking pin 12 into/from the first cylindrical cavity 72. Also, in the depressed state of the plunger the fitting 26 is not in contact with the O-ring 28. This unseals the open end of the second cylindrical cavity 74 via the unsealed contact between the posterior section 38 of the plunger 14 and the fitting 26.

Figure 3:
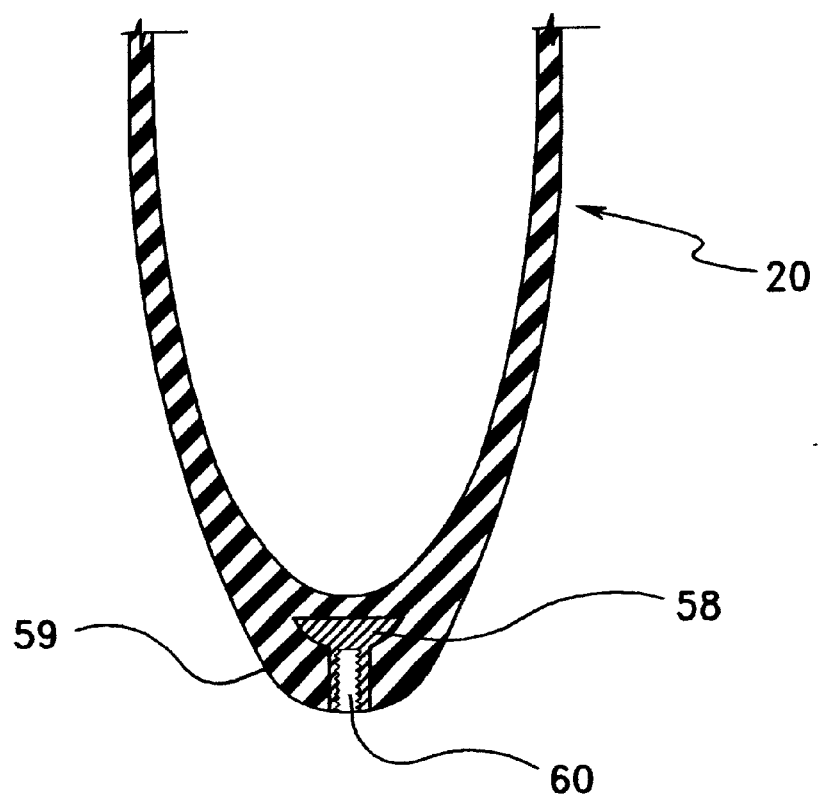
FIG. 3 is a sectional view of the socket liner of FIG. 1.

After the alignment and lamination procedures (to be described later herein) are concluded the safety suction valve 10 (FIGS. 1 and 2) is ready to be used by the patient. The laminated stump socket 22 (FIG. 1) and safety suction valve 10 are coupled to a lower limb prosthesis. The socket liner 20 (FIGS. 1, 3 and 9), which is preferably customized to the shape and size of the patient's residual limb, is sheathed on to the stump 78 (shown in FIG. 9) of the amputee. The locking pin 12 (FIG. 2) is coupled to the distal end 59 of the socket liner 20, preferably utilizing screw means which threadably engage the threaded hole 60 of the connector 58 of the socket liner 20 (FIG. 3). Further, the patient may also employ a cosmetic covering that encompasses the lower limb prosthesis, in which case the length of the posterior section 38 (FIG. 2) of the plunger 14 is adjustable to accommodate the cosmetic covering.

The safety suction valve 10 is very simply operated. With the plunger 14 of the safety suction valve 10 in the released state (see FIGS. 5A, 6A and 7A) the residual limb 78 clad with the socket liner 20 (FIG. 1), which has the locking pin 12 attached to its distal end 59 (FIG. 3), is inserted into the stump socket 22 (FIG. 1). During this insertion the socket liner 20 may, on one or more occasions, form a substantially circumferential seal with the inner surface of the stump socket 22 and impede the forward progress of the stump 78 into the stump socket 22 since the released state of the plunger 14 maintains the fluid integrity of the air inside the distal end of the stump socket 22. If this occurs the plunger 14 of the safety suction valve 10 is depressed (if the plunger 14 is substantially fully depressed then the plunger 14 is in the depressed state shown in FIGS. 5B, 6B and 7B) which allows air inside the distal end of the stump socket 22 to communicate with ambient atmospheric air via the cavities 72 and 74. This permits the stump 78 to continue its forward progress into the stump socket 22. When the stump 78 nears its end of travel inside the stump socket 22 the bottom part 52 of the locking pin 12 makes contact with the first cylindrical cavity 72 of the base 16. If the plunger 14 is in its released state (FIGS. 5A, 6A and 7A) it will not permit the bottom part 52 of the locking pin 12 to be fully inserted into the first cylindrical cavity 72 of the base 16. The plunger 14 is substantially fully depressed which results in the plunger 14 now being in the depressed state as shown in FIGS. 5B, 6B and 7B and this substantially synchronously permits the bottom part 52 of the locking pin 112 to be substantially fully inserted into the first cylindrical cavity 72 of the base 16 and allows air inside the distal end of the stump socket 22 to communicate with ambient atmospheric air. The plunger 14 is then released (FIGS. 5A, 6A and 7A) and this synchronously latches the locking pin 12 inside the first cylindrical cavity 72 of the base 16 and traps air inside the distal end of the stump socket 22 (at this stage of insertion the socket liner 20 has formed a substantially circumferential seal with the inner medial and/or proximal surface of the stump socket 22). This completes the donning of the stump socket 22.

In one preferred embodiment, the locking pin 12 (FIG. 2) includes one recess 56 so that it latches inside base 16 of the valve 10 in a substantially repeatable single position. This is desirable when the patient needs to repeatedly and consistently achieve substantially the same prosthetic configuration when the residual and artificial limbs are articulated. In other preferred embodiments, the locking pin 12 (FIG. 2) can include more than one recesses 56 so that it can latch at a plurality of positions in the base 16 of the valve 10, as dictated by the particular needs of the patient.

During use of the prosthesis the plunger 14 remains in its released state (FIGS. 5A, 6A and 7A), thereby retaining the prosthesis on the patient's residual limb 78 by a combination of mechanically locking the stump 78 to the prosthesis and by maintaining a suspending suctional force (reduced or negative pressure) between the stump 78 and the stump socket 22.

When the patient is ready to doff the stump socket the plunger 14 is fully depressed (FIGS. 5B, 6B and 7B), thereby unlatching the locking pin 12 from the base 16 and permitting air into the distal end of the stump socket 22 as the stump 78 is withdrawn from the stump socket 22. This unlatching and the release of suction allows the patient to easily extract the stump 78 from the stump socket 22.

Thus, the safety suction valve 10 provides a redundant support system for safety by reliably suspending an artificial limb from a residual limb. This is accomplished by the substantially synchronous activation of a latch and valve mechanism as described herein above. The latch mechanism provides a mechanical lock and the valve mechanism controls the pressure within the stump socket 22.

The safety suction valve 10 can be mounted to a lower limb prosthesis using any one of a number of conventional means, such as via pyramid adapters, alignment adapters and the like. However, it is preferred to provide a low-profile stem and alignment coupler to permanently and reliably secure the safety suction valve 10 to an artificial limb. Preferably, the stem 70 (FIG. 2) of the base 16 is a protruding structure at the lower surface of the base 16 and is attachable to an alignment coupler 18. The stem 70 preferably has a substantially square cross-section with rounded corners. Preferably, stem 70 has a length of about 0.5 inches and lateral dimensions of about 0.625 inches× 0.625 inches. Preferably, the stem 70 is fabricated from the same material as the base 16.

Figure 9:
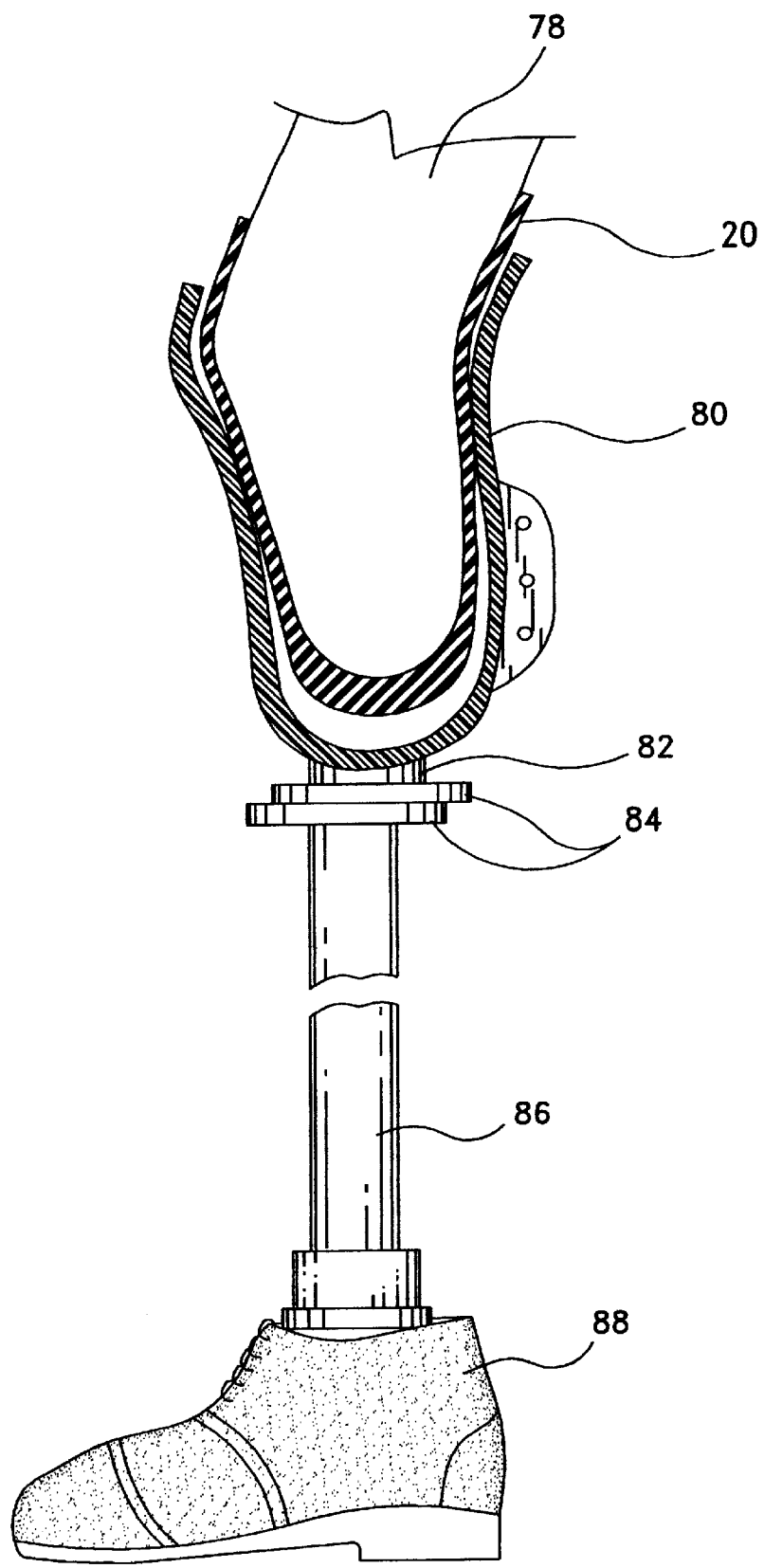
FIG. 9 illustrates an alignment method in accordance with a preferred embodiment of the present invention.

In one preferred embodiment of the invention the alignment coupler 18, shown in FIGS. 2 and 6, is a substantially square-shaped plate-like structure which is attachable, for example, by using screw means, to a lower limb prosthesis such as, for example, the prosthetic pylon 86 shown in FIG. 9. Preferably, the alignment coupler 18 has a substantially central substantially square-shaped hole 24 that tightly accommodates the stem 70 of the base 16, and a plurality of screw-receiving threaded holes 25 to attach the coupler 18 to a prosthesis. A substantially square-shaped cross-section is employed for the hole 24 since this prevents the possibility of any relative rotational movement between the alignment coupler 18 and the base 16, though it would be obvious to those of ordinary skill in the art that many other non-rotatably locking shapes may be utilized. The alignment coupler 18 is preferably fabricated from a low-cost, light-weight metal such as aluminum but other materials may be employed with efficacy, such as stainless steel, titanium, delrin or other plastics. Preferably, the alignment coupler 18 has a thickness of about 0.5 inches and lateral dimensions of about 2 inches×2 inches with the hole 24 having cross-sectional dimensions of about 0.625 inches×0.625 inches. This is advantageous since the modest thickness, preferably 0.5 inches, of the alignment coupler 18 adds minimally, preferably only 0.5 inches, to the overall length of the prosthesis which is desirable, especially to accommodate articulation between long stumps and artificial limbs.

Figure 8:
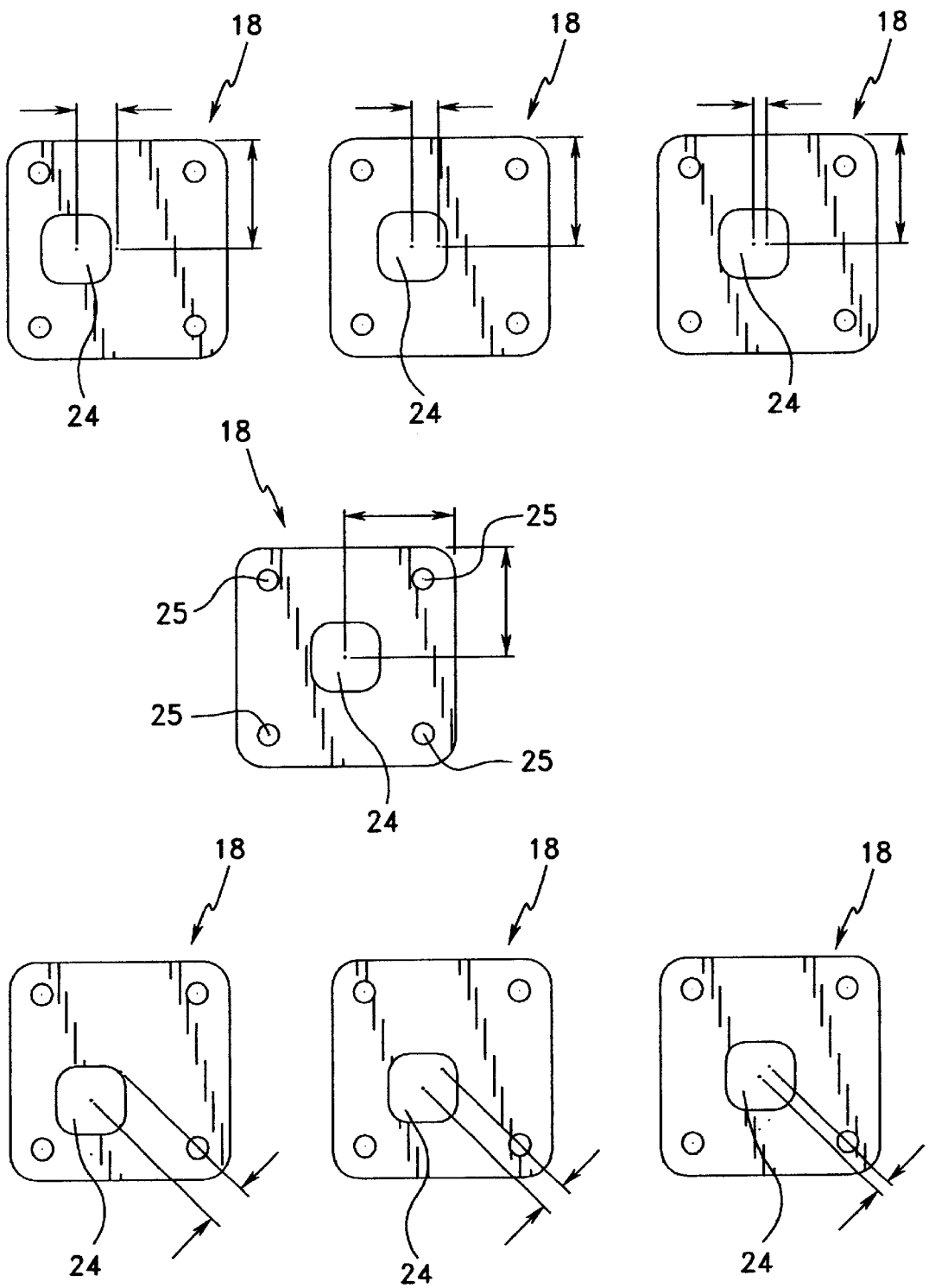
FIG. 8 illustrates a preferred alignment coupler kit including a plurality of alignment couplers of varying offset.

The hole 24 of the alignment coupler 18 is situatable in a multitude of eccentric locations, some of which are shown in FIG. 8, allowing for a plurality of alignment options between the residual limb of a patient and an artificial limb. FIG. 8 illustrates an alignment coupler kit including a plurality of alignment couplers 18 of varying offset. More specifically, FIG. 8 shows "seven" possible positions for the location of the hole 24 in the alignment coupler 18. Referring again to FIG. 8 it is seen that the hole 24 can be centered, can be laterally displaced off-center in three incrementing positions, and can be diagonally displaced off-center in three incrementing positions. Thus, it would appear that FIG. 8 illustrates "seven" alignment options but, in fact, FIG. 8 represents "twenty five" different alignment options utilizing "seven" different alignment couplers 18. This is true, since each alignment coupler 18 can have four different orientations with respect to the lower limb prosthesis. Thus, in addition to the one centered hole 24, each one of the six off-center holes 24 represent four alignment positions resulting in a total of "twenty five" different alignment options. Those skilled in the art will readily comprehend that by changing the shapes of the alignment coupler 18, the hole 24 and the stem 70 more or fewer orientations for the alignment coupler 18 may be realized resulting in more or fewer alignment options. Similarly, by placing the hole 24 in more or fewer positions in the alignment coupler 18 more or fewer alignment options can be achieved. The scope of the present invention encompasses all these different shapes for the alignment coupler 18, the hole 24 and the stem 70, and all possible positions for the hole 24. It has been found that the preferred substantially square shape for the alignment coupler 18, the hole 24 and the stem 70, and the "seven" positions for the hole 24 shown in FIG. 8 provide sufficient alignment options for most patients and are feasible for bulk manufacturing purposes, but some patients may require further consideration. In that case, custom alignment couplers can readily be fabricated to provide more precise alignment, where needed.

The above dimensions of the various components of the invention specified herein are illustrative for use with a normally sized adult. Those of ordinary skill in the art will readily comprehend that the invention may be modified, to scale it to be congruous to children of varying ages and adults/children of abnormal sizes, without departing from the scope of the invention.

The invention preferably employs a laminated stump socket 22 (see FIG. 1) the distal end of which is interfaceable with the groove 76, shown in FIG. 2, of the base 16 of the safety suction valve 10. The lamination 64 of the stump socket 22 preferably sealably substantially envelops the base 16 and the alignment coupler 18, as shown in FIG. 1, hence ensuring optimum coupling strength between the stump socket 22, base 16 and alignment coupler 18.

The present invention also provides a preferred method, best illustrated by FIG. 9, of aligning a stump or residual limb 78 to a lower limb prosthesis. In this method, stump 78 is sheathed with a socket liner 20 (also shown in FIGS. 1 and 3) and placed in a test socket 80. Preferably, the test socket 80 is fabricated from a clear hard plastic and is substantially contoured around the stump 78. The distal end of the test socket 80 has a plate 82 which permits threadable attachment of the test socket 80 to a lower limb prosthesis. Preferably, before the test socket 80 is donned by the amputee, the test socket 80 has already been coupled, utilizing an adjustable coupler 84, to a prosthetic pylon 86 which in turn is articulated to a prosthetic foot 88. The adjustable coupler may be any of a number of commercially available prosthetic alignment devices (for example, one manufactured by Durr-Fillauer of Chattanooga, Tenn.) which employ two slidably engaged plates. The stump 78 is aligned with the prosthetic pylon 86 by adjusting the relative lateral displacement between the plates of the adjustable coupler 84. The alignment procedure using the adjustable coupler 84 involves a trial-and-error type methodology, in which the initial step is a visual alignment followed by appropriate adjustments as the patient employs the prosthesis to engage in mobile ambulation activities such as walking, pacing or running. In the present invention, the adjustable coupler 84 merely serves the purpose of determining the correct alignment between the stump 78 and the prosthetic pylon 86 and unlike conventional techniques is not incorporated as a permanent feature in a lower limb prosthesis. The potential hazards of using such an adjustable coupler 84 in a prosthetic device have already been discussed hereinabove.

Once the stump 78, as shown in FIG. 9, is properly aligned with respect to the prosthetic pylon 86 the relative directional offset between the stump 78 and the prosthetic pylon 86 is measured. Further, the positioning of the threaded hole 60 in the connector 58 of the socket liner 20 (see FIG. 3) in relation to the distal end of the test socket 80 is noted. Advantageously, since the test socket 80 is fabricated from a clear material any nonconformities, if present, in the fitting of the test socket 80 to the stump 78 are noted and recorded.

The stump 78 (FIG. 9) is removed from the test socket 80 and a cast 90 (FIG. 10) of the stump 78 is fabricated based on the fit of the stump 78 in the test socket 80. Preferably, a laminated stump socket (as shown in FIG. 1) is manufactured and coupled with the safety suction valve 10, though a conventional thermoplastic stump socket may be utilized as well with efficacy.

Figure 10:
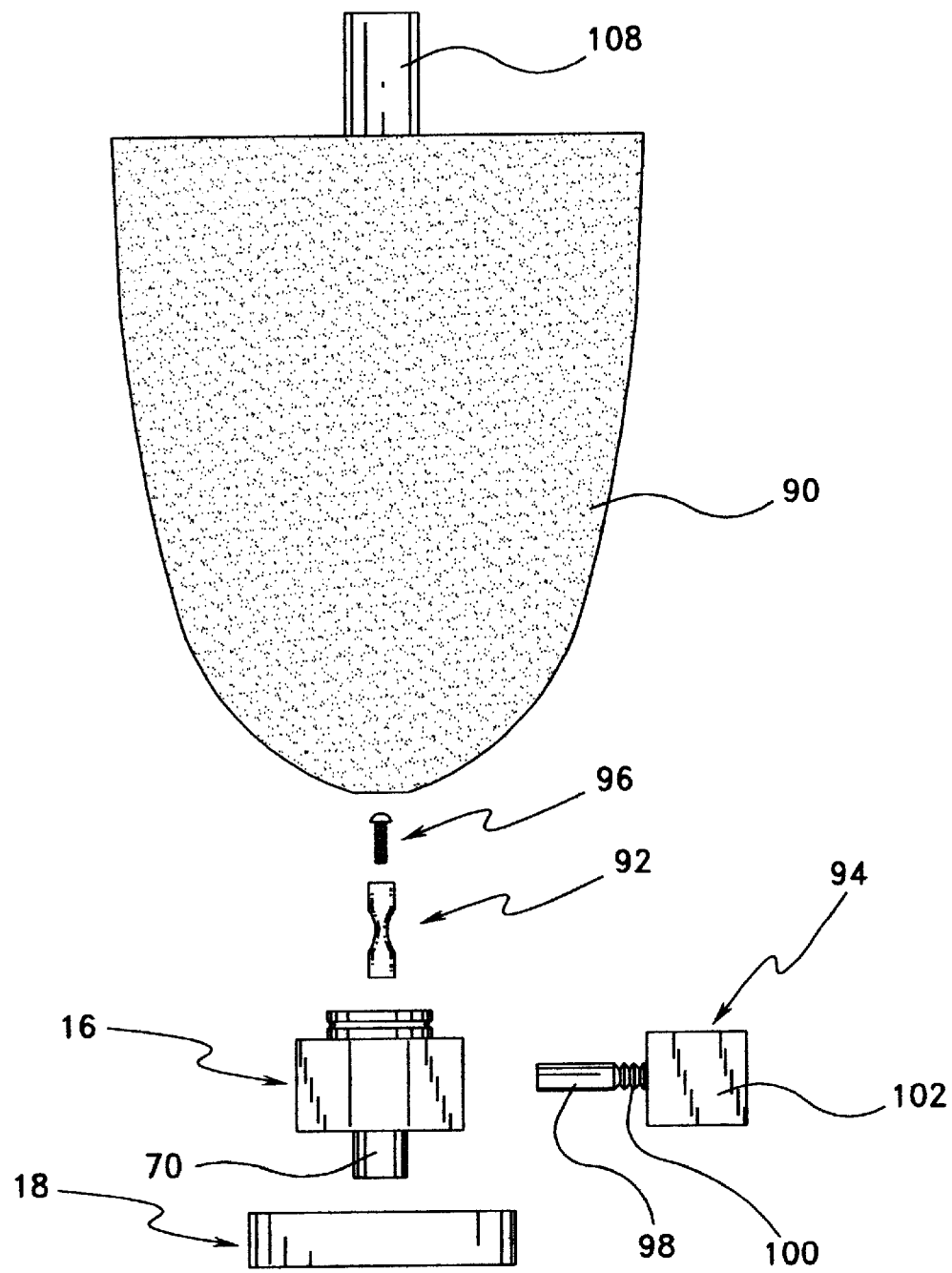
FIG. 10 illustrates a lamination procedure in accordance with a preferred embodiment of the present invention.

A preferred lamination procedure is illustrated in FIG. 10 and utilizes the cast 90, the base 16, the alignment coupler 18, a dummy pin 92 and a dummy plunger 94. The dummy pin 92 is preferably shaped and sized substantially similar to the bottom part 52 of the locking pin 12 (see FIG. 2) except that its top part is threaded to entertain a screw 96. Preferably, the dummy plunger 94 has a front cylindrical portion 98 with threads 100 that is threadably attachable in the second cylindrical cavity 74 (see FIG. 2) of the base 16, and a back portion 102. With the screw 96 attached to the dummy pin 92 the dummy pin 92 is inserted into the first cylindrical cavity 72 (see FIG. 2) and the dummy plunger 94 is threaded into the second cylindrical cavity 74 (see FIG. 2). This locks the dummy pin 92 into the base 16.

Referring to FIG. 10, the distal end of the cast 90 preferably has a hole at a position substantially corresponding to the afore-determined position of the threaded hole 60 in the connector 58 of the socket liner 20 (see FIG. 3) in relation to the test socket 80 (see FIG. 9). With the dummy pin 92 locked into the base 16 and the screw 96 attached to the dummy pin 92, the screw 96 is inserted and glued into the hole at the distal end of the cast 90 such that the top of the base 16 is in substantially flush contact with the distal end of the cast 90. This removably couples the base 16 with the cast 90. If desired, a putty-like material may be employed at the junction of the base 16 with the distal end of the cast 90 to prevent contamination during the lamination process.

Figure 11:
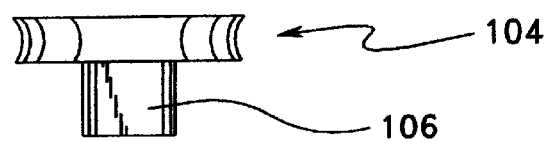
FIG. 11 illustrates an alternative embodiment of the base member of the present invention.

Alternatively, the base 16 (FIG. 10) may be replaced by a base member 104 as shown in FIG. 11. The base member 104 is interfaceable with the distal end of a stump socket (for example, the laminated stump socket 22 shown in FIG. 1) and has a stem 106 that is fittable in the hole 24 of the alignment coupler 18 (see FIG. 2). Thus, those skilled in the art will readily recognize that the alignment mechanism of the present invention may be practiced with or without the inclusion of the "latch" and "valve" mechanisms of the safety suction valve 10.

With reference to FIGS. 2, 8 and 10, an appropriate alignment coupler 18 is fitted on to the stem 70. Preferably, one of the alignment couplers 18 depicted serves the purpose, but if not, a customized alignment coupler 18 with the hole 24 in the required location may be used. The choice of the appropriate alignment coupler is based on the predetermined relative offset between the stump 78 and the prosthetic pylon 86 (see FIG. 9). Preferably, screws are inserted into the threaded holes in the alignment coupler 18 to prevent contamination by the resin during the lamination procedure. The dummy pin 92 and the dummy plunger 94 also serve in the capacity of protecting the first cylindrical cavity 72 and the second cylindrical cavity 74 (see FIG. 2) of the base 16 from the resin during lamination.

The stump socket 22 is laminated over the cast 90 and the lamination also sealably substantially envelops the assembly of the base 16, the alignment coupler 18, the dummy pin 92 and the dummy plunger 94 (FIG. 10). Preferably, the lamination is a graphite-epoxy composite lamination though other fiber-resin compositions may be utilized with efficacy. Once the lamination is complete, access is provided to the end of the back portion 102 of the dummy plunger 94 by stripping off a patch of the lamination. Preferably, the back portion 102 is latchable to a fastening element which is used to unscrew and remove the dummy plunger 94 from the base 16. After removal of the dummy plunger 94 from the base 16 the dummy pin 92 is no longer locked to the base 16 but is still attached to the cast 90 via the screw 96. The cast 90 preferably has a rod 108 embedded in it during its fabrication. The rod 108 is gripped and subjected to an axial pulling force which removes the cast 90, with the dummy pin 92 attached to its distal end, from the lamination leaving the first cylindrical cavity 72 (see FIG. 2) of the base 16 accessible at the interior distal end of the stump socket 22 (FIG. 1). The screws inserted into the threaded holes of the alignment coupler 18 are removed and the assembly of the plunger 14, the spring 30, the fitting 26 and the O-ring 28 are affixed to the second cylindrical cavity 74 (FIG. 2) of the base 16.

The preferred alignment method described herein, advantageously, permits prealignment of the prosthesis before the lamination during a single patient examination. Conventional alignment transfer may require the lamination to be performed before the alignment, and this can undesirably result in two examinations of the patient.

Figure 12:
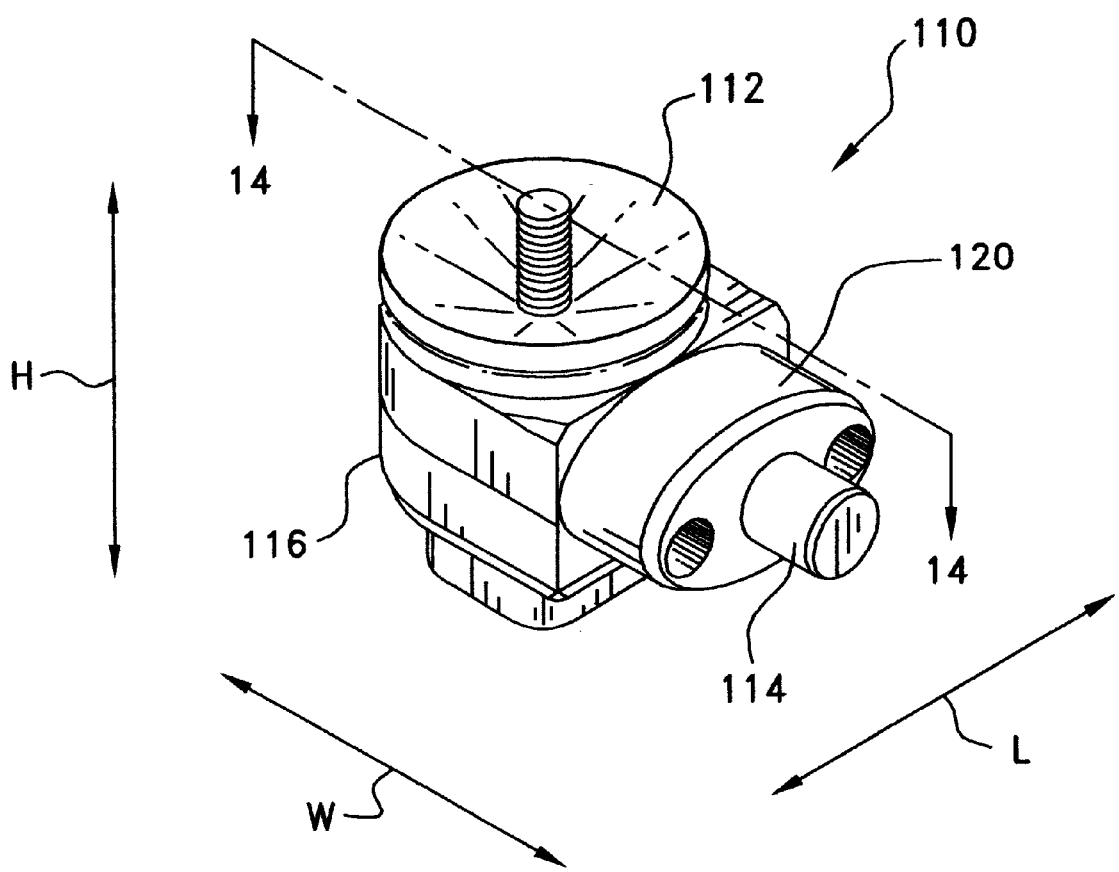
FIG. 12 is a perspective view of a safety suction valve in accordance with another preferred embodiment of the present invention.
Figure 13:
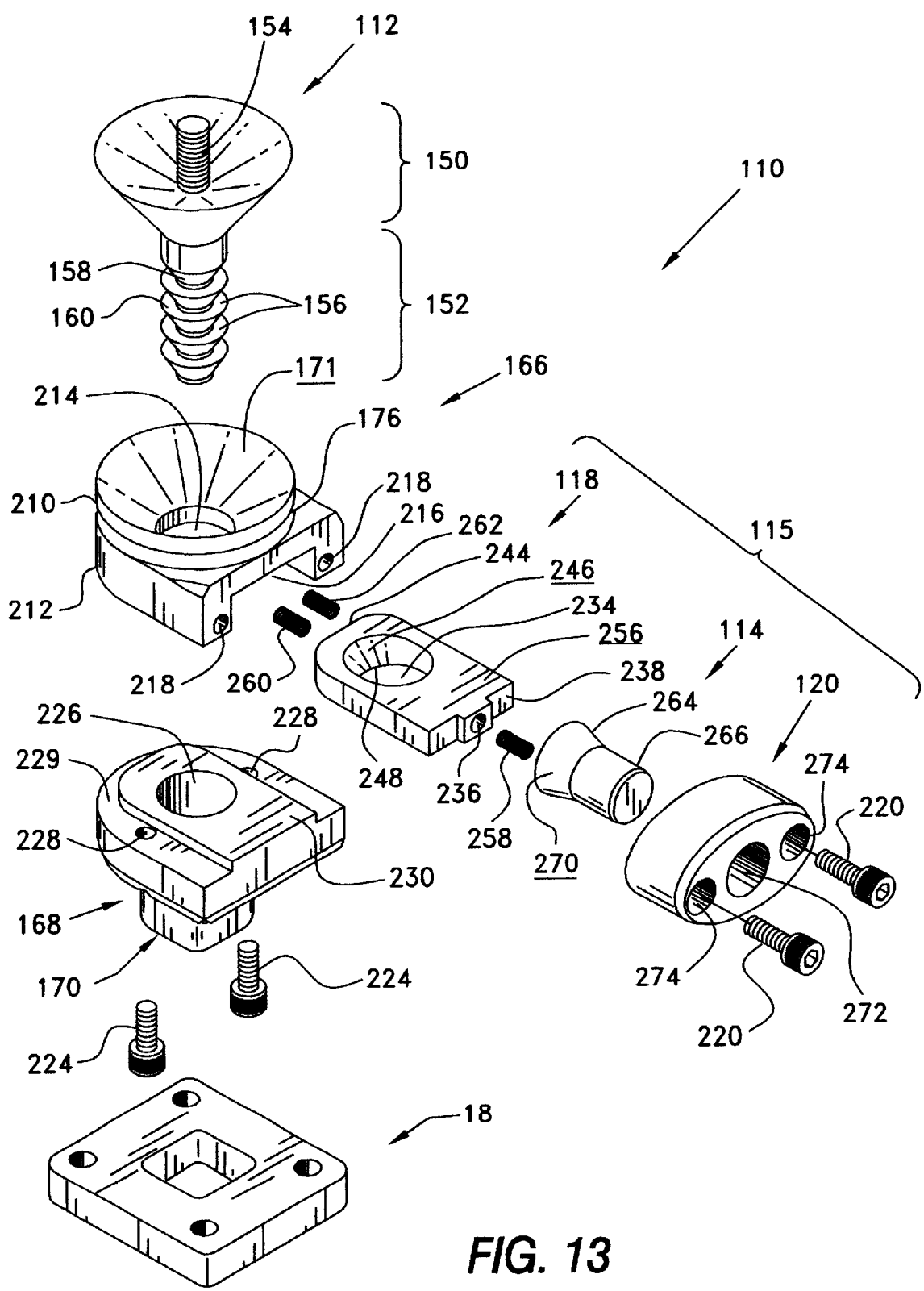
FIG. 13 is an exploded perspective view of the safety suction valve of FIG. 12.

FIGS. 12 and 13 show another preferred embodiment of a safety suction valve or lock 110 constructed and assembled in accordance with the present invention. The valve 110 generally comprises a locking pin 112, a plunger 114, a base 116, a latching plate 118, and a plunger mount 120. The locking pin 112 includes a top part 150 and a bottom part 152. Preferably, the top part 150 of the locking pin 112 has a substantially frusto-conical shape with a concave upper surface in which a screw 154 is embedded. The screw 154 is preferably adapted to connect the locking pin 112 to the socket liner 20 (FIG. 3), though any one of a number of suitable socket liners may be utilized. Preferably, the screw 154 threadably engages the connector 58 (see FIG. 3) at the distal end 59 of the socket liner 20 and, hence, couples the locking pin 112 to the socket liner 20. The bottom part 152 of the locking pin 112 is generally elongated and cylindrical, and includes one or more annular recesses, notches or grooves 156. Employing several of these notches 156 can form a barb-like bottom part 152. The bottom part 152 of the locking pin 112 is latchable in the base 116 as will be discussed at greater length later herein. In one preferred embodiment, the recess 156 is created by the intersection of a generally frusto-conical central tapered surface 158 and an outer ring-shaped surface 160, though the recesses 156 may be shaped in various other manners with efficacy, giving due consideration to the goal of reliably latching the locking pin 112 into the base 116 of the valve 110. Preferably, the locking pin 112 is fabricated from a light-weight durable material, for example, delrin plastic, although various other suitable materials may be used with efficacy, as required or desired, such as aluminum, titanium, Nylon or other plastics, among others.

The base 116 (FIG. 2) preferably includes an upper part 166, a middle part 168 and a stem 170 at the lower surface of the middle part 168. The upper part 166 of the base 116 includes a generally cylindrical top portion 210 and a generally U-shaped bottom portion 212. The top portion 210 preferably includes a groove 176 which facilitates interfacement of the base 116 with the distal end of a stump socket, for example the socket 22 (FIG. 1). Preferably, the top portion 210 has a substantially bowl-shaped interior surface 171 for receiving the top part 150 of the locking pin 112. The surface 171 terminates in a generally cylindrical cavity 214 of the bottom portion 212. The cavity 214 preferably has a diameter slightly larger than the maximum diameter of the bottom part 152 of the locking pin 112 so that the bottom part 152 is insertable into the cavity 214, and a gap is provided for air flow. The bottom portion 212 of the base upper part 166 includes a generally rectangular slot 216 that is in communication with the cavity 214. The bottom portion 212 also includes a pair of threaded holes 218 for threadably engaging a pair of screws 220 to attach the plunger mount 120 to the base 116. The lower surface 221 (see FIG. 17) of the bottom portion 212 also includes a pair of threaded holes 222 for threadably engaging a pair of screws 224 (FIG. 13) to attach the base upper part 166 to the base middle part 168. Alternatively, the base upper part 166 and the base middle part 168 may be attached by other means, for example, by utilizing pins, clamps, locks or adhesives among other attachment means. The base upper part 166 and the base middle part 168 may also be formed as an integral unit.

Figure 16:
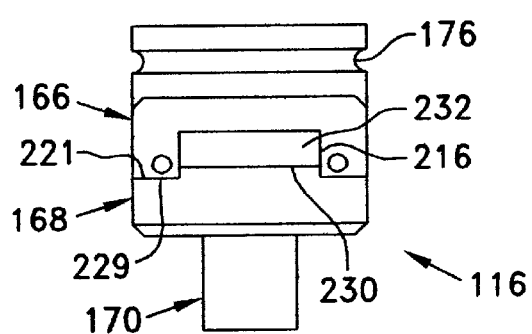
FIG. 16 is a side elevational view of the base of FIG. 12.
Figure 17:
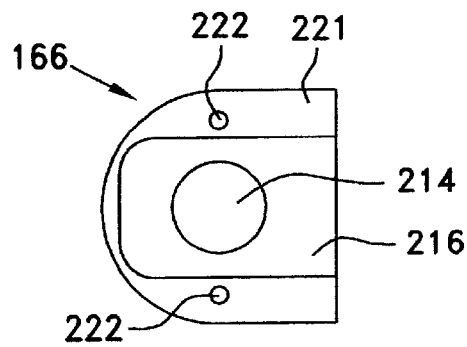
FIG. 17 is a bottom plan view of the upper portion of the base of FIG. 12.
Figure 18D:
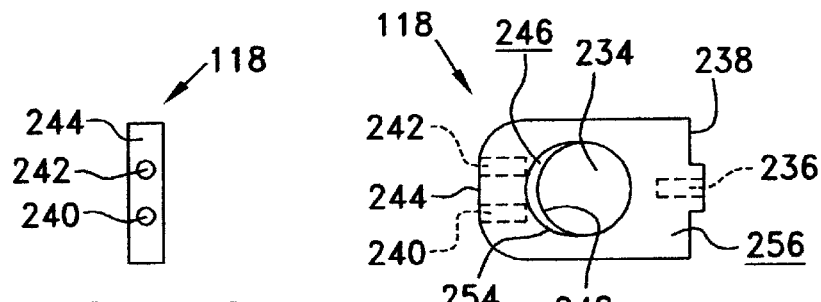
FIG. 18D is a bottom plan view of the latching plate of FIG. 13.
Figure 18D:
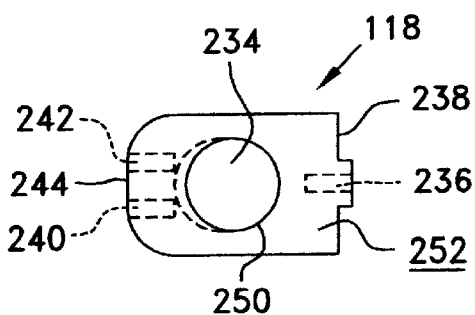
Figure 19A:
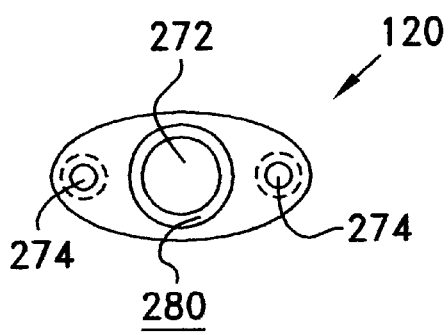
FIG. 19A is a front elevational view of the plunger mount of FIG. 12.
Figure 19C:
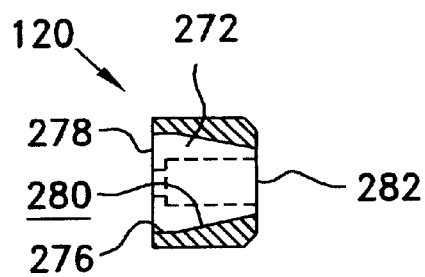
FIG. 19C is a sectional view taken along line 19C—19C of FIG. 19B.
Figure 19B:
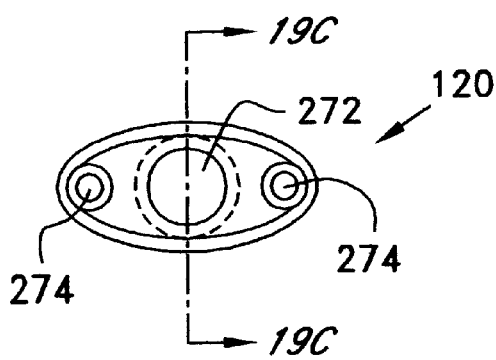
FIG. 19B is a back elevational view of the plunger mount of FIG. 12.

Referring to FIG. 13, preferably the middle part 168 of the base 116 is generally U-shaped. Preferably, the middle part 168 includes a generally cylindrical cavity 226, a pair of counterbored through holes 228, and a generally rectangular raised section 230. The cavity 226 preferably has a diameter slightly larger than the maximum diameter of the bottom part 152 of the locking pin 112 so that the bottom part 152 is insertable into the cavity 226. The screws 224 traverse the holes 228 and threadably engage the threaded holes 222 (FIG. 17) of the base upper part 166 to attach the base middle part 168 and the base upper part 166. When the base upper part 166 and base middle part 168 are attached, the cavities 214 and 226 are in substantial alignment with one another. Also, and referring to FIG. 16, the raised section 30 mates with the slot 216 to define a lateral chamber 232 for receiving the latching plate 118. Referring to FIGS. 13, 16 and 17, preferably, the base upper part lower surface 221 and the base middle part surface 229 are smooth enough to sealingly interface with one another. Optionally, sealing means such as a suitable gasket or silicone may be used to provide a seal at the interface between the base upper part lower surface 221 and the base middle part surface 229. Preferably, the base 116 is fabricated from a light-weight durable material, for example, delrin plastic, although various other materials may also be used with efficacy, as required or desired, such as aluminum, titanium, Nylon or other plastics, among others.

The safety suction valve 110 (FIGS. 12 and 13) can be mounted to a lower limb prosthesis using any one of a number of conventional means, such as via pyramid adapters, alignment adapters and the like. However, it is preferred to provide a low-profile stem and alignment coupler to permanently and reliably secure the safety suction valve 110 to an artificial limb. Preferably, the stem 170 of the base 116 is a protruding structure at the lower surface of the base 116 and is fabricated from the same material as the base 116. The stem 170 is attachable to the alignment coupler 18. A discussion of the alignment coupler 18 and alignment method has already been presented herein above, and hence shall not be repeated here for the sake of brevity.

Referring to FIGS. 13 and 18A to 18D, preferably, the latching plate 118 is generally rectangular in shape. The latching plate 118 includes a latching hole 234, a spring-receiving cavity 236 at a back end 238, and a pair of spring-receiving cavities 240, 242 at a front end 244. The latching hole 234 preferably has a tapered surface 246 to define a protruding edge 248, a generally circular opening 250 at a lower surface 252 of the latching plate 118, and a generally oval opening 254 at an upper surface 256 of the latching plate 118. The tapered surface 246 and/or the protruding edge 248 are adapted to latch or lock into the locking pin 112, as discussed later herein. The spring-receiving cavities 236, 240, 242 are preferably adapted to receive respective coil springs 258, 260, 262 to effectively spring-load the plunger 114. In other embodiments, alternative resilient means such as other types of springs or resilient materials may be used with efficacy, as required or desired, to resiliently load the plunger 114. The latching plate 118 is configured and dimensioned to be received in the chamber 232 (FIG. 16) of the base 116 with some clearance space to allow lateral movement of the latching plate 118 and to provide gaps to allow air to enter or escape from the suction valve 110, as discussed below. The latching hole 234 is in at least partial alignment with the base cavities 214 and 226. Preferably, the latching plate 118 is fabricated from a light-weight durable material, for example, delrin plastic, although various other materials may also be used with efficacy, as required or desired, such as aluminum, titanium, Nylon or other plastics, among others.

Figure 20A:
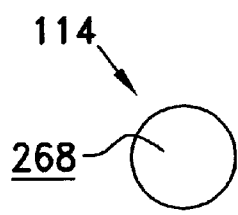
FIG. 20A is a front elevational view of the plunger of FIG. 12.
Figure 20B:
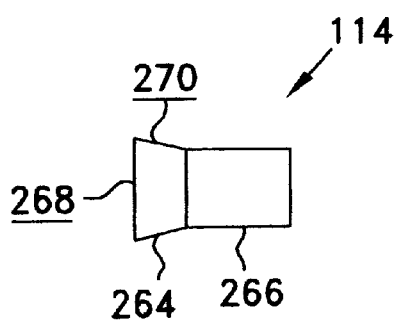
FIG. 20B is a side elevational view of the plunger of FIG. 12.
Figure 20C:
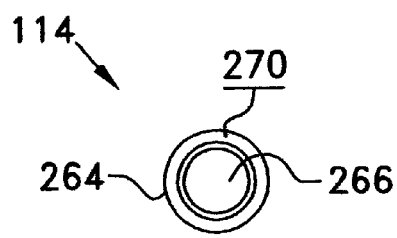
FIG. 20C is a back elevational view of the plunger of FIG. 12.

Referring to FIGS. 13 and 20A to 20B, the plunger 114 preferably includes an anterior section 264 and a posterior section 266. The latching plate 118, the plunger 114, the plunger mount 120, and the springs 258, 260, 262 form a plunger assembly 115. The anterior section 264 has a generally circular front face 268 (FIG. 20A) and a generally frusto-conical tapered surface 270. The plunger front face 268 is in communication with the spring 258, and hence the latching plate 118. The posterior section 266 of the plunger 114 is generally cylindrical in shape. The plunger 114 is used to displace the latching plate 118, as discussed later herein. Preferably, the plunger 114 is fabricated from a light-weight durable material, for example, delrin plastic, although various other materials may also be used with efficacy, as required or desired, such as aluminum, titanium, Nylon or other plastics, among others.

The plunger mount 120 (FIG. 13, 19A to 19C) includes a plunger-receiving cavity 272 and a pair of counterbored through holes 274. Preferably, the cavity 272 has a generally cylindrical flat portion 276 extending from a generally circular front opening 278 and a generally frusto-conical tapered surface 280 terminating in a generally circular back opening 282. The tapered surface 280 of the plunger mount 120 is adapted to sealingly mate with the tapered surface 270 of the plunger 114 in the "released" plunger position, that is at the at rest or normal plunger position, as discussed later herein. Optionally, other suitable means such as an O-ring or gasket may be utilized to provide an effective seal. The back opening 282 has a diameter slightly larger than the diameter of the plunger posterior section 266 to allow the posterior section 266 to extend through the back opening 282 and to provide some clearance space for air to enter or escape from the suction valve 110, as discussed later herein. The screws 220 traverse the holes 274 and threadably engage the threaded holes 218 of the base upper part 166 to attach the plunger mount 120 and the base 116. Alternatively, the plunger mount 120 and the base 116 may be attached by other means, for example, by utilizing pins, clamps or locks among other attachment means. Preferably, the plunger mount 120 and base 116 contacting surfaces are smooth enough to sealingly interface the plunger mount 120 with the base 116. Optionally, sealing means such as an O-ring, a suitable gasket or silicone may be used to provide a seal at the interface between the plunger mount 120 and the base 116. Preferably, the plunger mount 120 is fabricated from a light-weight durable material, for example, delrin plastic, although various other materials may also be used with efficacy, as required or desired, such as aluminum, titanium, Nylon or other plastics, among others.

The safety suction valve 110 (FIGS. 12 and 13) may be dimensioned in various ways to accommodate varying sizes of patients, giving due consideration to the goals of providing reliable suspension of an artificial limb from a residual limb. In one preferred embodiment, the safety suction valve 110 has an overall height H in the range from about 1 inch to about 2½ inches, a width W in the range from about 2 inches to about 21/2 inches, a length L in the range from about 1 inch to about 1½ inches.

Figure 14A:
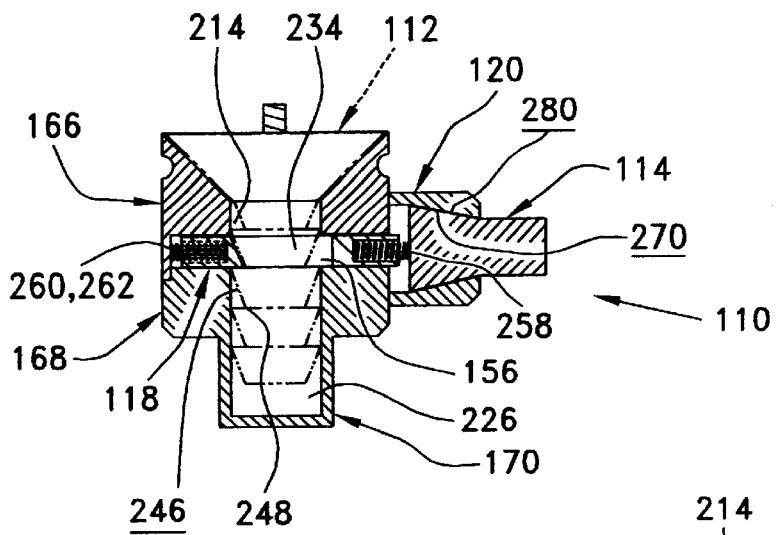
FIG. 14A is a sectional view along line 14—14 of FIG. 12 illustrating a "released" plunger position.

The plunger 114 has a "released" state, as shown in FIGS. 14A and 1SA, in which the latching plate tapered surface 246 and protruding edge 248 extend inwards relative to the cylindrical cavities 214 and 226 to lock or latch into the groove or recess 156 of the locking pin 112 (shown in phantom). The released state is the normal, unperturbed or rest state of the safety suction valve 110. The latching of the tapered surface 246 and/or edge 248 in the locking pin 112 presents a physical obstruction to the removal/insertion of the locking pin 112 from/into the valve 110. In the released state the coil springs 258, 260, 262 are partially compressed to provide enough of a spring bias or push to force the plunger tapered surface 270 to sealingly mate with the plunger mount tapered surface 280.

Figure 14B:
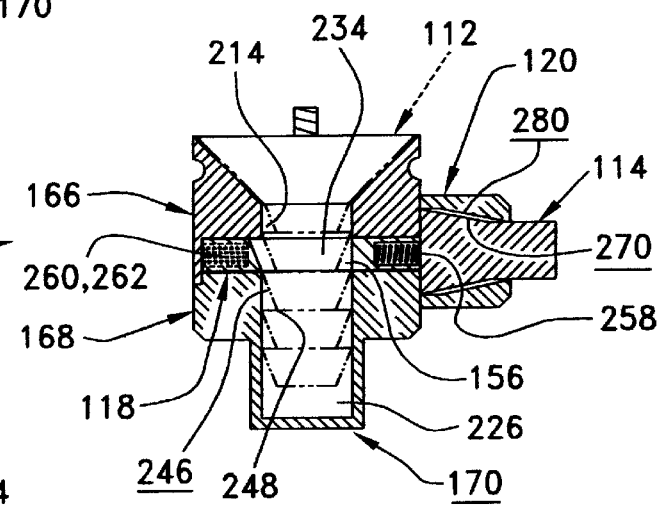
FIG. 14B is a sectional view taken along line 14—14 of FIG. 12 illustrating a "depressed" plunger position.

The plunger 114 has a "depressed" state, as shown in FIGS. 14B and 16B, in which the latching plate tapered surface 246 and protruding edge 248 do not extend substantially inwards relative to the cylindrical cavities 214 and 226 to unlock or unlatch from the groove or recess 156 of the locking pin 112 (shown in phantom). The depressed state is achieved by depressing, preferably manually, the plunger 114 of the safety suction valve 110. This displaces the plunger 114 inwards causing further compression of the springs 258, 260, 262 until the plunger 114 and/or the latching plate 118 reach their end-of-travel. The displacement of the latching plate 118 removes the physical obstruction, provided by the tapered surface 246 and protruding edge 248, which allows removal/insertion of the locking pin 112 from/into the valve 110. The displacement or depression of the plunger 112 also breaks the sealed mating between the plunger tapered surface 270 and the plunger mount tapered surface 280.

The safety suction valve 110 (FIGS. 12 and 13) can be used by the patient after the alignment of the prosthesis is concluded. In one preferred embodiment, the alignment utilizes the alignment coupler kit of FIG. 9 and the alignment method as illustrated by FIG. 10. The stem 170 (FIGS. 12 and 13) of the valve 110 (FIGS. 12 and 13) is substantially the same as the stem 70 (FIG. 2) of the valve 10 (FIG. 2). Since the alignment components and methodology have already been discussed herein above, in conjunction with the stem 70 (FIG. 2) of the valve 10 (FIG. 2), the discussion will not be repeated here for the sake of brevity.

In one preferred embodiment, a laminated stump socket (as shown in FIG. 1) is manufactured and coupled with the safety suction valve 110, though a conventional thermoplastic stump socket may be utilized as well with efficacy, as required or desired. The socket lamination procedure (FIG. 10) has been discussed herein above in conjunction with the safety suction valve 10 (FIG. 2). A substantially similar lamination procedure can be utilized in conjunction with the valve 110 (FIGS. 12 and 13) utilizing a suitably configured dummy pin 92 (FIG. 10) and dummy plunger 94 (FIG. 10) to accommodate the valve base 116 and/or other components of the safety suction valve 110 (FIGS. 12 and 13). Hence, the discussion of the stump lamination shall not be repeated here for the sake of brevity.

The following description of the use of the safety suction valve 110 (FIGS. 12 and 13) is described by referring to the laminated stump socket 22 (FIG. 1), the socket liner 20 (FIGS. 1 and 3), and the stump 78 (FIG. 9). After the alignment and lamination procedures, the laminated stump socket 22 (FIG. 1) and safety suction valve 110 (FIGS. 12 and 13) are coupled to a lower limb prosthesis. The socket liner 20 (FIGS. 1 and 3), which is preferably customized to the shape and size of the patient's residual limb, is sheathed on to the stump 78 (shown in FIG. 9) of the amputee. The locking pin 112 is coupled to the distal end 59 of the socket liner 20, preferably utilizing screw means which threadably engage the threaded hole 60 of the connector 58 of the socket liner 20 (FIG. 3). Further, the patient may also employ a cosmetic covering that encompasses the lower limb prosthesis, in which case the length of the posterior section 266 of the plunger 114 is adjustable to accommodate the cosmetic covering.

Figure 15A:
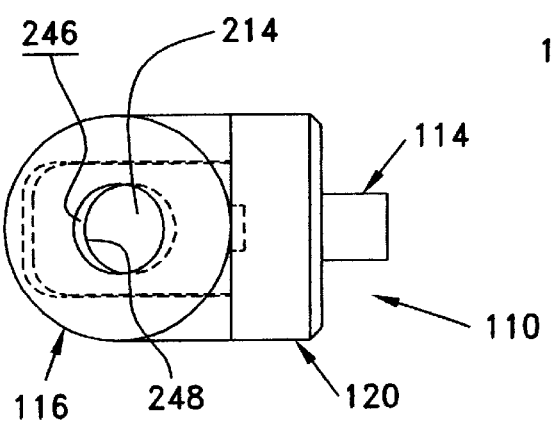
FIG. 15A is a top plan view of the safety suction valve of FIG. 12 with the locking pin removed to illustrate a "released" plunger position.
Figure 15B:
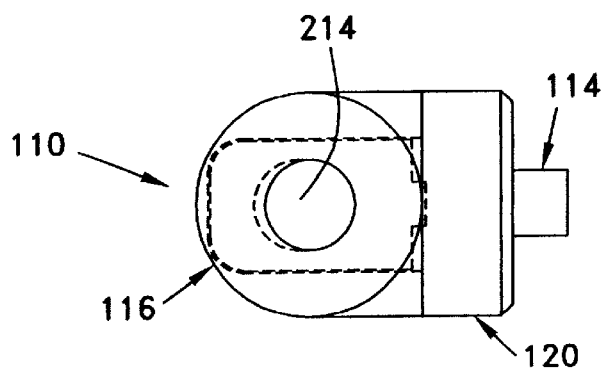
FIG. 15B is a top plan view of the safety suction valve of FIG. 12 with the locking pin removed to illustrate a "depressed" plunger position.

The safety suction valve 110 (FIGS. 12 and 13) is simple to operate. With the plunger 114 of the safety suction valve 110 in the released state (FIGS. 14A and 15A) the residual limb 78 (FIG. 9) clad with the socket liner 20 (FIGS. 1 and 3), which has the locking pin 112 attached to its distal end 59 (FIG. 3), is inserted into the stump socket 22 (FIG. 1). During this insertion the socket liner 20 may, on one or more occasions, form a substantially circumferential seal with the inner surface of the stump socket 22 and impede the forward progress of the stump 78 into the stump socket 22 since the released state of the plunger 114 maintains the fluid integrity of the air inside the distal end of the stump socket 22. If this occurs the plunger 114 of the safety suction valve 110 is depressed (if the plunger 114 is substantially fully depressed then the plunger 114 is in the depressed state shown in FIGS. 14B and 15B) which allows air inside distal end of the stump socket 22 to communicate with ambient atmospheric air via the base cavity 214, the base chamber 232 (FIG. 16) and the plunger mount cavity 272. This permits the stump 78 to continue its forward progress into the stump socket 22. When the stump 78 nears its end of travel inside the stump socket 22 the bottom part 152 of the locking pin 112 makes contact with the latching hole 234 of the latching plate 118. If the plunger 114 is in its released state (FIGS. 14A and 15A) it will not permit the bottom part 152 of the locking pin 112 to be inserted through the latching hole 234 of the latching plate 118. The plunger 114 is substantially fully depressed which results in the plunger 114 now being in the depressed state as shown in FIGS. 14B, 15B, and this substantially synchronously permits the bottom part 152 of the locking pin 112 to be inserted into the cavity 226 of the base 116 and allows air inside the distal end of the stump socket 22 to communicate with ambient atmospheric air. The plunger 114 is then released (FIGS. 14A and 15A) and this substantially synchronously latches the locking pin 112 inside the valve 110 and traps air inside the distal end of the stump socket 22 (at this stage of insertion the socket liner 20 has formed a substantially circumferential seal with the inner medial and/or proximal surface of the stump socket 22). This completes the donning of the stump socket 22.

In one preferred embodiment, the locking pin 112 (FIG. 13) includes one recess 156 so that it latches inside the base 116 of the valve 110 in a substantially repeatable single position. This is desirable when the patient needs to repeatedly and consistently achieve substantially the same prosthetic configuration when the residual and artificial limbs are articulated. In other preferred embodiments, the locking pin 112 (FIG. 13) can include more than one recesses 156 so that it can latch at a plurality of positions in the base 116 of the valve 110, as dictated by the particular needs of the patient.

During use of the prosthesis the plunger 114 remains in its released state (FIGS. 14A and 15A), thereby retaining the prosthesis on the patient's residual limb 78 (FIG. 9) by a combination of mechanically locking the stump 78 to the prosthesis and by maintaining a suspending suctional force (reduced or negative pressure) between the stump 78 and the stump socket 22 (FIG. 1).

When the patient is ready to doff the stump socket the plunger 114 is substantially fully depressed (FIGS. 14B and 15B), thereby unlatching the locking pin 112 from the valve 110 and permitting air into the distal end of the stump socket 22 as the stump 78 is withdrawn from the stump socket 22. This unlatching and the release of suction allows the patient to easily extract the stump 78 from the stump socket 22.

In this manner, the safety suction valve 110 (FIGS. 12 and 13) provides a redundant support system for safety by reliably suspending an artificial limb from a residual limb. This is accomplished by the substantially synchronous activation of a latch and valve mechanism as described herein above. The latch mechanism provides a mechanical lock and the valve mechanism controls the pressure within the stump socket 22. One goal of the valve 110 of the present invention is to provide a light-weight component that does not substantially add to the weight of the overall prosthesis.

The safety suction valve of the present invention releasably secures a residual limb to an artificial limb. The safety suction valve substantially synchronously activates a latch mechanism (by mechanically locking on to a socket liner) and a valve mechanism (by controlling the air flow in and out of the distal end of a stump socket), hence providing superior retention of a residual limb in a stump socket and resulting in ease of donning and doffing of a stump socket by an amputee. Thus, the safety suction valve provides a redundant support system for safety by reliably suspending an artificial limb from a residual limb. The consolidation of the latch and valve mechanisms is an improved feature of the present invention. Moreover, the safety suction valve is an inexpensive, simple and light-weight device that is conveniently operated by the patient. One preferred embodiment of the invention further includes an alignment mechanism and prescribes an alignment method which result in a reliable and accurate alignment between a residual limb and an artificial limb.

While the various components and methods of the present invention have been described with a certain degree of particularity, it is manifest that many changes may be made in the specific designs, constructions and methodology hereinabove described without departing from the spirit and scope of this disclosure. It is understood that the invention is not limited to the embodiments set forth herein for purposes of exemplification, but is to be defined only by a fair reading of the appended claims, including the full range of equivalency to which each element thereof is entitled.

What is claimed is:

1. A valve and latch combination for a limb prosthesis, comprising:
    a. a locking pin adapted to be attached to a distal end of a limb socket liner;
    b. a base adapted to be attached to a distal end of a limb socket, said limb socket being adapted to receive and support said limb socket liner;
    c. a latch within said base for releasably receiving and securing said locking pin;
    d. a valve also within said base for regulating air pressure between said limb socket liner and said limb socket; and,
    e. a plunger which cooperates with said base to actuate both said latch and said valve.

2. The valve and latch combination of claim 1 wherein said latch adjustably secures said locking pin.

3. The valve and latch combination of claim 1 wherein said plunger synchronously actuates said latch and said valve.

* * * * *